United States Patent [19]

Ramioulle et al.

[11] 4,155,919

[45] May 22, 1979

[54] PROCESS FOR THE PRODUCTION OF 1,4-BUTANEDIOL AND TETRAHYDROFURAN

[75] Inventors: Jean Ramioulle, Bierghes; Willy Couteau, Brussels, both of Belgium

[73] Assignee: U C B Societe Anonyme, Belgium

[21] Appl. No.: 853,566

[22] Filed: Nov. 21, 1977

[30] Foreign Application Priority Data

Nov. 23, 1976 [GB] United Kingdom ............... 48795/76

[51] Int. Cl.$^2$ ..................... C07D 307/08; C07C 27/04
[52] U.S. Cl. ................................. 260/346.11; 568/864
[58] Field of Search ...................... 260/346.11, 635 D; 568/864

[56] References Cited

U.S. PATENT DOCUMENTS

| | | | |
|---|---|---|---|
| 2,772,291 | 11/1956 | McShane et al. | 260/346.11 X |
| 2,772,293 | 11/1956 | Gilbert et al. | 260/346.11 X |
| 3,492,314 | 1/1970 | Asano et al. | 260/346.11 X |
| 3,890,361 | 6/1975 | Kanetaka et al. | 260/346.11 X |

FOREIGN PATENT DOCUMENTS

| | | | |
|---|---|---|---|
| 49-56888 | 4/1974 | Japan | 260/346.11 |
| 49-46978 | 5/1974 | Japan | 260/346.11 |
| 49-32439 | 8/1974 | Japan. | |
| 1200979 | 8/1970 | United Kingdom. | |

*Primary Examiner*—Richard Raymond
*Attorney, Agent, or Firm*—Wenderoth, Lind & Ponack

[57] ABSTRACT

Process for the catalytic hydrogenolysis of maleic anhydride to give 1,4-butanediol and tetrahydrofuran in a single-stage operation by means of hydrogen under heat and pressure, in the presence of a suspension of a reduced solid catalyst, which contains as catalytically active elements Ni in association with Mo and/or W and optionally with Zr and/or Nb, having the following essential characteristics: (I) double oxidizing treatment of the solid catalyst in two stages before its reduction, and (II) conducting the hydrogenolysis of maleic anhydride at a temperature of from 170° to 215° C. under a hydrogen pressure below about 200 bars, in a reaction medium which contains gamma-butyrolactone, for a time such that the amount of gamma-butyrolactone in the final reaction medium is substantially equal to that present in the initial reaction medium.

24 Claims, No Drawings

PROCESS FOR THE PRODUCTION OF 1,4-BUTANEDIOL AND TETRAHYDROFURAN

The present invention is concerned with a new process for the production of 1,4-butanediol and tetrahydrofuran from maleic anhydride by catalytic hydrogenolysis of maleic anhydride in a single-stage operation.

It is known that, depending on the state of advance of the reaction, catalytic hydrogenolysis of maleic anhydride gives rise to the formation of a series of compounds in accordance with the following reaction scheme:

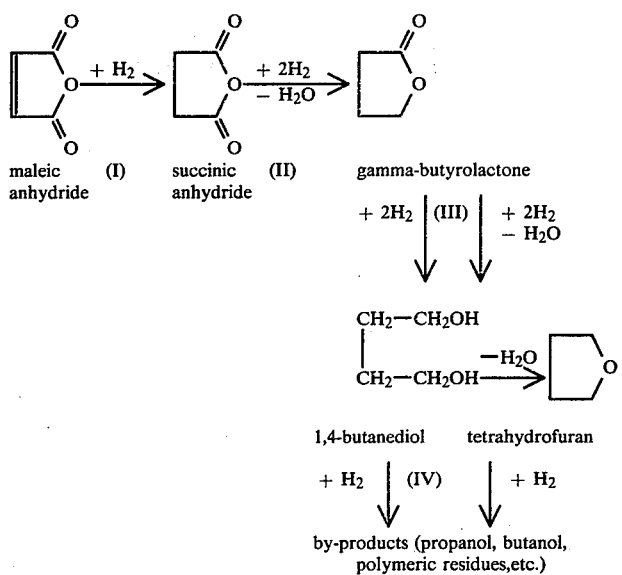

This scheme clearly shows that the desired products according to the present invention, i.e. 1,4-butanediol (BD) and tetrahydrofuran (THF) are intermediate hydrogenolysis products of maleic anhydride obtained in accordance with reactions (I), (II) and (III) and that, in order to obtain them, it is necessary for the conversion process to be stopped in time, failing which less valuable by-products will be obtained, such as propanol, butanol and the like (reaction IV).

Furthermore, assuming that it is possible to stop at the hydrogenolysis stage BD+THF, if it is desired to promote the formation of BD to the detriment of THF or vice versa, it must be possible to influence the reaction selectively in the desired direction.

The successive and/or parallel hydrogenolysis reactions indicated above in the scheme each have their own reaction conditions. For example, the hydrogenation of maleic anhydride to give succinic anhydride requires only a relatively low pressure and temperature, whereas the hydrogenolysis of succinic anhydride to give butyrolactone requires considerably higher pressures and temperatures. It is for this reason that, in order to obtain optimum yields, most patent literature in this field relates to determined partial stages of the reaction scheme given above, for example the conversion of maleic anhydride into succinic anhydride and butyrolactone (published Japanese Patent Applications Nos. 17,259/67 and 17,818/67), or the conversion of butyrolactone into BD or into THF (published Japanese Patent Applications Nos. 5366/69 and 72407/70). More recently, according to Belgian Pat. No. 835,269, the complete process is effected in three separate stages: (a) maleic anhydride→succinic anhydride, (b) succinic anhydride→butyrolactone and (c) butyrolactone→butanediol and/or tetrahydrofuran.

It will be understood that if this procedure can be justified for the purpose of obtaining higher yields of desired products, its major disadvantage is, nevertheless, the fact that it entails a considerable expense for installation (three reactors and an intermediate distillation separation column between stages (b) and (c) in the case of Belgian Pat. No. 835,269).

Furthermore, a characteristic common to all these processes is that, in at least one stage of the chain of reactions, it is necessary to employ high pressures, amounting to hundreds of bars, which accordingly increases the cost of installation and operation.

Finally, in order that these various reactions can be carried out at the lowest possible temperatures, use is made either of catalysts containing elements, the cost of which is very high (for example rhenium, thorium or the like), or of catalysts which are highly reactive but very sensitive to poisoning, which necessitates very elaborate purification processes for the materials which are to be hydrogenolyzed.

It is for this reason that it would be of the greatest technical and economic interest to be able to effect the conversion of maleic anhydride into 1,4-butanediol and/or tetrahydrofuran by a single-stage process, operating with inexpensive equipment, under relatively low pressures and in the presence of a stable catalyst, the cost of which is acceptable, while, nevertheless, obtaining good yields of the desired products.

As far as we are aware, the literature cites only one concrete case of direct conversion of maleic anhydride into 1,4-butanediol in a single stage in the presence of a nickel-cobalt-thorium catalyst in which the remarkable yield of 82% of theory is obtained (published Japanese Patent Application No. 32,439/74). Unfortunately, a major disadvantage of this process is the catalyst used. It is well known that thorium is a radioactive element, which requires strict precautions for handling, transport and use. Furthermore, thorium is relatively expensive and, in addition, its use is, at the present time, subject to regulations issued by official organizations in the nuclear field, in the same way as uranium. Furthermore, the production of this catalyst requires calcination temperatures which may be as high as 1000° C. Finally, according to the practical examples quoted in this Patent Application, the hydrogenolysis of the maleic anhydride is carried out at pressures of from 200 to 300 bars and at reaction temperatures as high as 270° C.; consequently, if this process were to be applied on the industrial scale, it would require very elaborate and, consequently, very expensive engineering.

It is for this reason that we have carried out research work with the object of developing a process for the synthesis of 1,4-butanediol and tetrahydrofuran by the hydrogenolysis of maleic anhydride in a single stage, which process, unlike, in particular, the process of the above-mentioned published Japanese Patent Application No. 32,439/74 could be applied easily and economically on an industrial scale, because:

(a) an active catalyst which is inexpensive and has a low sensitivity to poisoning would be used and which dues not raise ecological problems during preparation and use;

(b) the reaction would be carried out in a simple apparatus, the construction and operation of which would not be prohibitively expensive, in view of the fact that it would be required to operate under pressures below 200 bars and preferably below 125 bars and at reasonably high temperatures;

(c) nevertheless, very good yields of BD+THF (of 90 mol percent and more) would be obtained, while it would be possible for the molar ratio of BD/THF in the reaction product obtained to be varied selectively.

These three objects are achieved by the process according to the present invention, which is distinguished by the following essential characteristics:

(I) use of a special catalyst of the Ni/Mo and/or Ni/W type, optionally containing zirconium and/or niobium, which has undergone oxidizing treatment in two stages before the reducing treatment;

(II) conducting the catalytic hydrogenolysis of maleic anhydride in the presence of the catalyst described in (I) in suspension at a temperature of from 170° to 215° C. at a pressure below 200 bars and preferably below 125 bars, in a solvent medium containing gamma-butyrolactone, for a time such that the concentration of gamma-butyrolactone in the final product is brought back to its concentration in the starting reaction medium.

Thus, according to the present invention there is provided a process for the catalytic hydrogenolysis of maleic anhydride to give 1,4-butanediol and tetrahydrofuran in a single-stage operation by means of hydrogen under heat and pressure, in the presence of a suspension of a reduced solid catalyst, which contains as catalytically active elements nickel in association with molybdenum and/or tungsten and optionally with zirconium and/or niobium, which comprises:

(I) subjecting the solid catalyst to oxidation in two stages before its reduction, and (II) effecting the hydrogenolysis of maleic anhydride at a temperature of from 170° to 215° C. under a hydrogen pressure below about 200 bars and preferably below about 125 bars, in a reaction medium which contains gamma-butyrolactone, for a time such that the amount of gamma-butyrolactone in the final reaction medium is substantially equal to that present in the initial reaction medium.

This is not the first time that nickel, cobalt, molybdenum, tungsten, chromium and like catalysts, either in the form of oxides or in metallic form, have been proposed for the catalytic hydrogenation of dicarboxylic anhydrides (see U.S. Pat. Nos. 2,772,291; 2,772,292 and 2,772,293; and British Pat. No. 1,200,979); however, the hydrogenation products thus obtained are cyclic lactones (for example gamma-butyrolactone) and/or cyclic ethers (for example tetrahydrofuran but in much smaller amounts), with the practically complete absence of the formation of the corresponding diols (for example 1,4-butanediol). Consequently, these catalysts cannot be used according to the present invention for obtaining high yields of 90% and more of BD+THF. Furthermore, the catalysts of the above-mentioned U.S. patent specifications rapidly lose their activity (see British Pat. No. 1,200,979, page 1, lines 25 to 39). Furthermore, the difference between the catalyst of British Pat. No. 1,200,979 and those used in the present invention, which results in obtaining different products in the hydrogenolysis of dicarboxylic anhydrides, probably arises from the fact that in this Patent the compounds of nickel and molybdenum and/or tungsten are directly reduced, without previously passing through the two-stage formation of the corresponding oxides as proposed in the present invention. Whatever explanation can be given, it is found that the products of the hydrogenolysis of maleic anhydride in the presence of the catalysts of British Pat. No. 1,200,979 contain a maximum of 86.6 mol % of gamma-butyrolactone (Table 2, page 6 of that patent), a maximum of 18.1 mol % of tetrahydrofuran (Table 1, page 4 of that patent) and also small amounts of n-propanol, n-butanol, propionic acid, succinic anhydride and succinic acid, without the formation of 1,4-butanediol. On the contrary, the reaction products obtained according to the present invention contain up to 75 mol % of 1,4-butanediol and up to 50 mol % of tetrahydrofuran, without any appreciable formation of additional gamma-butyrolactone.

In the following, there is described the catalyst and the method of catalytic hydrogenolysis according to the present invention:

(I) CATALYSTS (I.1.) Raw materials

The catalytically active elements contained in the catalysts used in the present invention are nickel, molybdenum and/or tungsten and optionally zirconium and/or niobium. The raw materials used for the preparation of these catalysts are compounds which are soluble in water and which, by thermal reduction, can supply the elements nickel, molybdenum and/or tungsten, zirconium and/or niobium in metallic form. Compounds of this kind include, for example, the following:

nickel: nitrate, formate, oxalate, tartrate, citrate and the like;

molybdenum: ammonium paramolybdate, molybdate and the like;

tungsten: ammonium tungstate, silicotungstic acid and the like;

zirconium: zirconium oxychloride and the like;

niobium: niobium hydroxide, oxalate and the like.

Although the catalysts can be used without a support material, for obvious reasons of economy, it is preferred to use supported catalysts. The support material used may be, for example, pumice, silica, aluminum silicate, alumina, kieselguhr or the like, preference being given in increasing order to aluminum silicate, alumina and kieselguhr.

(I.2) Preparation of the catalysts

The first step is the impregnation of the catalyst support by agitation with an aqueous solution of the nickel salt at ambient temperature. In order to improve the adhesion of the nickel salt to the support and to increase the amount of the former absorbed by the latter, the nickel salt can be precipitated in the form of the carbonate, by adding an appropriate amount of ammonium carbonate. If the nickel salt used is the nitrate, the impregnated support is then carefully washed in order to free it from the ammonium nitrate thus formed, which could give rise to explosions in the subsequent thermal treatments. Whereas, if a nickel salt other than the nitrate is used, for example an oxalate, there is obviously no reason why the impregnated support should not also be washed but this operation is not necessary.

The supported nickel carbonate is then subjected to an oxidation treatment by heating in the presence of air at a temperature of from 200° to 500° C. for a period of from 1 to 10 hours and preferably at a temperature of from 350° to 500° C. for a period of 2 to 4 hours. After this first oxidizing treatment, the nickel contained in the support is substantially converted into the oxide state.

The catalyst support impregnated with nickel oxide is allowed to cool and is then mixed with an aqueous solution of the molybdenum and/or tungsten compound. The supported catalyst material is then dried and calcined in the presence of air (second oxidizing treatment) at a temperature of 300° to 700° C. for a time of from 1 to 20 hours and preferably at a temperature of from 450° to 550° C. for a time of 2 to 4 hours. Below 300° C. and a treatment time of 1 hour, there is a reduction both of the life and of the activity of the catalysts obtained because the respective oxides of the catalyst elements used are not well formed. On the other hand, above 700° C. a distinct drop in activity is observed due to the decreased specific surface area. Furthermore, starting from an oxidizing treatment time of 20 hours, we have found that the useful life of the catalysts is not further improved and that, on the contrary, the catalytic activity tends to decrease. It is for this reason that the preferred conditions are a temperature close to 500° C. and a treatment time of about 3 hours (see Example 1).

If it is desired to increase the proportion of tetrahydrofuran in the product of the catalytic hydrogenolysis of maleic anhydride, the required amount of water-soluble compound of zirconium and/or niobium should, in addition, be added either to the nickel salt solution or to the molybdenum and/or tungsten salt solution (see Example 5).

It will be noted that the double oxidizing treatment described above, which is a characteristic of the present invention, is essential in order to obtain not only goods yields of 1,4-butanediol and tetrahydrofuran but also a long active life of the catalysts obtained in this manner (see Example 8).

At the end of this oxidizing treatment, the air is driven off and replaced by an inert gas atmosphere and then direct reduction of the catalyst is effected in an atmosphere of hydrogen at a temperature of from 450° to 500° C. for 1 to 20 hours and preferably for about 3 hours. When the reduction has been completed, one of the two following methods may be used for the storage of the catalyst obtained in this manner:

(a) the catalyst is cooled to about 100° C. and the hydrogen atmosphere is replaced by an atmosphere of carbon dioxide, followed by cooling to ambient temperature, whereafter the atmosphere of carbon dioxide is progressively replaced by air, or (b) the reduced catalyst is cooled to ambient temperature in an atmosphere of hydrogen and the catalyst is kept in the solvent which will subsequently be used as the reaction medium for the conversion of maleic anhydride into 1,4-butanediol and tetrahydrofuran.

Of these two methods, method (b) is preferred for the purposes of the present invention.

(I.3.) Composition and properties of the catalysts

In the catalysts used in the present invention, the atomic ratio Mo:Ni or W:Ni is between 0.03 and 0.3, preferably between 0.1 and 0.2 and in particular between 0.11 and 0.13.

In cases where it is desired to increase the proportion of THF in the THF+BD mixture obtained by using the process of the present invention, compounds of zirconium and/or niobium are added in the preparation of the catalysts in such an amount that the atomic ratio Zr:Ni and/or Nb:Ni is from 0.001 to 0.1

The catalysts are in the form of solid particles having a particle size lower than 240 microns. Their specific surface area is at least 100 $m^2/g$ and at most 165 $m^2/g$; if the specific surface area is lower than 100 $m^2/g$, catalytic activity is too low, while if it exceeds 165 $m^2/g$, the selectivity in respect of 1,4-butanediol decreases and, at the same time, there is a rapid decrease of useful life due to progressive sintering of the surface of the catalyst particles. It is for that reason that, in a preferred embodiment of the process of the present invention, the catalysts have a specific surface area of preferably about 140 to about 150 $m^2/g$.

When the catalysts are supported catalysts, the weight ratio between the total amount of catalytically active material (calculated in the form of metal) and the amount of support is preferably so selected that the catalysts contain from 20 to 99% by weight and more preferably about 40 to about 60% by weight of catalytically active material.

(II) CATALYTIC HYDROGENOLYSIS of MALEIC ANHYDRIDE

According to the present invention, the catalytic hydrogenolysis of maleic anhydride is carried out by heating under pressure in the presence of hydrogen and of the above-described catalyst in suspension. It is known that maleic anhydride is a substance which is solid at ambient temperature (m.p. about 52.5° C.). For the application of the process of the present invention by the technique of hydrogenolysis in the presence of a catalyst in suspension, it is possible to effect this operation by using only maleic anhydride fed in a molten state. However, this procedure gives rise to difficulties because maleic anhydride sublimes when heated so that there is a risk of the formation of depositions on the cold parts of the apparatus and obstruction of pipes, particularly in cold weather, when the manufacturing installation is built in the open air. For this reason, according to a preferred form of the process of the present invention, the catalytic hydrogenolysis of maleic anhydride is carried out in solution in an appropriate solvent medium. This medium is composed of gamma-butyrolactone alone or in admixture with dioxan and/or tetrahydrofuran.

Referring to the reaction scheme given initially, it will be seen that reaction (III) leads to the formation of 1,4-butanediol and tetrahydrofuran and that reaction (IV) destroys the 1,4-butanediol and tetrahydrofuran with the formation of by-products of little value, such as propanol and butanol.

The hydrogenolysis should, therefore, be stopped at the moment when the content of 1,4-butanediol and tetrahydrofuran passes through a maximum. At this moment, the reaction mixture will contain 1,4-butanediol, tetrahydrofuran, gamma-butyrolactone and a minor amount of by-products already formed by reaction (IV).

We have also observed that the content of gamma-butyrolactone in the reaction medium increases in dependence on time, passes through a maximum and then decreases again. According to the present invention, we have found that the moment when the content of gamma-butyrolactone has fallen back to its value in the initial reaction mixture coincides substantially with the moment when the content of 1,4-butanediol and tetrahydrofuran passes through a maximum. After separation of the butanediol and tetrahydrofuran as products of the process, the gamma-butyrolactone is recovered from the reaction mixture and re-used an unlimited number of times in subsequent hydrogenolysis operations carried out under the same conditions. Since, in each of these operations, the same amount of gamma-butyrolactone is recovered at the end of hydrogenolysis as the amount initially introduced, this means that the yield of gamma-butyrolactone is zero and that the maleic anhydride used as starting material is converted to the extent of up to about 90 mol % into 1,4-butanediol and tetrahydrofuran, without further formation of gamma-butyrolactone every time the process is repeated.

The hydrogenolysis could obviously be conducted in such a manner that the content of gamma-butyrolactone at the moment when the hydrogenolysis is interrupted will be lower than it was at the beginning of the hydrogenolysis, thus increasing the amount of 1,4-butanediol and tetrahydrofuran formed. However, at the same time, the formation of by-products would be increased, which would constitute a loss of material not capable of re-conversion into useful products, whereas if the hydrogenolysis is stopped at the moment when the gamma-butyrolactone in the reaction mixture has returned to its initial concentration, the amount of gamma-butyrolactone remaining intact as compared with the case described above can be reconverted to the extent of up to at least 90 moles % into 1,4-butanediol and tetrahydrofuran in the course of the next manufacturing batch. Similarly, the hydrogenolysis could be stopped before the gamma-butyrolactone content has returned to its initial value but this procedure would be uneconomical because of the larger amounts of gamma-butyrolactone to be recycled in comparison with the smaller amount of 1,4-butanediol and tetrahydrofuran produced.

An important factor in the process of the present invention is the weight ratio between the maleic anhydride and the amount of gamma-butyrolactone initially present in the reaction mixture. We have found that if the relative amount of gamma-butyrolactone is increased, the reaction time will be reduced, the yield of 1,4-butanediol will increase but the productivity of the reaction apparatus will decrease. On the other hand, if the relative amount of gamma-butyrolactone is reduced, the reaction time increases, the yield decreases but the productivity of the reaction apparatus increases. A relative amount of gamma-butyrolactone should, therefore, be selected which is a satisfactory compromise between these two opposed tendencies.

According to the present invention, the ratio by weight of maleic anhydride to gamma-butyrolactone in the initial reaction medium should be between 0.5:1 and 4:1 and preferably between 0.8:1 (see Example 4) and 2:1 (see Example 7). When, according to the present invention, the reaction medium contains dioxan and/or tetrahydrofuran as co-solvents, in addition to gamma-butyrolactone, the ratio by weight of gamma-butyrolactone to co-solvent is within the range from 1:0 to 1:7, preferably from 1:2 to 1:4.

According to a first embodiment, a solvent medium is used which, from the outset, contains gamma-butyrolactone and co-solvent in the weight ratio indicated above for the hydrogenolysis of maleic anhydride.

However, in another embodiment, the hydrogenolysis of maleic anhydride can be carried out solely in the presence of the co-solvent and the required amount of gamma-butyrolactone can be produced in situ. From the reaction medium thus produced, the amount of 1,4-butanediol and tetrahydrofuran formed is separated and an appropriate amount of maleic anhydride is added thereto in order then to operate in accordance with the first embodiment (see Example 3).

Although dioxan is remarkably suitable as reaction medium (see Example 2), nevertheless it constitutes an extraneous substance which must be removed from the reaction product at the end of the operation. For this reason, preference is given to gamma-butyrolactone and to tetrahydrofuran, because these two compounds are normally present in the hydrogenolysis of maleic anhydride.

Furthermore, the amount of catalyst used in carrying out the process of the present invention may vary between 10 and 40 parts by weight and preferably between 20 and 40 parts by weight per 100 parts by weight of maleic anhydride.

An essential advantage, from the technological point of view, of the process of the present invention is that it is carried out at pressures lower than 200 bars and preferably lower than 125 bars, which permits the use of conventional reactors and instruments which are convenient and economical in operation and in respect of maintenance. The operating pressure may, therefore, vary between 60 and 200 bars and preferably between 75 and 125 bars. In the method selected for industrial operation, it is advantageously between about 90 and 100 bars.

An essential operational feature of the process of the present invention is also the maintenance of a hydrogenolysis temperature between 170° and 215° C. and preferably between 200° and 210° C. We have found that, when operating above 215° C., the yields of desired products decrease, while when operating below 170° C., the speed of reaction decreases, thus necessitating a longer reaction time and leading to a reduction of the productivity of the reaction apparatus.

At the present time, numerous equipments exist which, with complete safety, permit operation under the reaction conditions described above. By way of example, mention is made of the so-called loop reactors, which comprise a pressure reactor provided with appropriate agitation means (screw, turbine or the like) connected externally to a circuit comprising a recycling pump and a heat exchanger. By appropriately adjusting the recycling rate of the reaction mixture and the temperature of the cooling fluid in the heat exchanger, it is possible for the reaction mixture to be kept easily and reliably at the operational temperature indicated.

According to the present invention, the process of catalytic hydrogenation of maleic anhydride into BD and THF can, for example, be effected in the following manner:

The desired amount of maleic anhydride, solvent and catalyst are introduced into a loop reactor, the reactor is then flushed out with nitrogen, the nitrogen is then replaced by hydrogen at a pressure of 50 bars and the agitation and heating means are put into operation. As soon as the temperature reaches 200° C., additional hydrogen is introduced in order to keep the reaction pressure constant at about 95 bars throughout the reaction period. The temperature is kept at 200°–210° C. by appropriate regulation of the rate of circulation of the reaction mixture and of the cooling fluid in the heat exchanger. The reaction time is regulated so as to obtain 100% conversion of the maleic anhydride and the highest possible yields of BD and THF in the manner explained above. Depending upon the operating parameters selected, the reaction time is between 4 and 12 hours and preferably between 4 and 6 hours. At the end of the reaction, the contents of the autoclave are cooled and relieved of pressure, the catalyst is filtered off and the filtrate is recovered. If it is found that the catalyst has undergone a loss of activity, it is partly replaced by fresh catalyst to restore its activity before it is re-used in another operation. Furthermore, the filtrate is subjected to separation, for example distillation, in order to recover the 1,4-butanediol, the tetrahydrofuran and the reaction medium (containing gamma-butyrolactone), the latter being then re-used indefinitely for subsequent productions.

In the process according to the present invention, it is easily possible to achieve 100% conversion of maleic anhydride, a yield of 1,4-butanediol as high as about 75 mol % and a yield of tetrahydrofuran as high as about 50 mol %, these yields varying in dependence on the operating parameters adopted. Only a small amount of secondary products (propanol, butanol) is formed, amounting to less than 10 mol % and advantageously less than 7 mol %.

The following Examples are given for the purpose of illustrating the present invention:

EXAMPLE 1

(a) Preparation of a catalyst for obtaining high yields of butanediol in the reaction product.

120 g nickel nitrate hexahydrate ($Ni(NO_3)_2.6H_2O$) are dissolved in 100 g distilled water and 20 g kieselguhr, the particle size of which is lower than 200 microns, are added thereto. Mixing is continued for 1 hour, a dark green suspension thereby being obtained. 40 g ammonium carbonate dissolved in 40 g distilled water are then added thereto portionwise, with agitation, a yellowish-green suspension thereby being formed which is filtered off. The filter cake is washed twice with distilled water and the residue is dried in an oven at 110°–120° C. for 16 hours.

A powder is thus obtained which is calcined in the presence of air for 3 hours at 450° C. It is allowed to cool to ambient temperature and the pulverulent composition is impregnated with 8.75 g ammonium paramolybdate $(NH_4)_6Mo_7O_{24}.4H_2O$ dissolved in 40 ml distilled water. The composition is kneaded and dried at 110°–120° C. for 24 hours. It is then calcined at 500° C. for 3 hours, allowed to cool to 475° C., flushed out with nitrogen at that temperature and the nitrogen is then replaced by hydrogen. Treatment with hydrogen is effected for 3 hours at 475° C. and the resulting catalyst is cooled to 20° C. in an atmosphere of hydrogen and immersed in the solvent used later on as reaction medium (either gamma-butyrolactone or gamma-butyrolactone mixed with dioxan and/or tetrahydrofuran, as the case may be) for the hydrogenolysis of maleic anhydride. Hereinbelow, this catalyst is designated "catalyst A". This catalyst has a specific surface area of 150 m²/g, contains 59.8% by weight of catalytically active material and has a Mo:Ni atomic ratio of 0.12.

(b) Preparation of a catalyst for obtaining higher yields of tetrahydrofuran in the reaction product.

The operation is exactly the same as for the preparation of catalyst A but, in addition to the 8.75 g ammonium paramolybdate, niobium oxalate in aqueous solution is added in such an amount as to give an atomic ratio of niobium to nickel of 0.01. The subsequent treatment is exactly identical with that described for catalyst A. This niobium catalyst is hereinafter referred to as "catalyst B". The specific surface area of this catalyst is 140 m²/g.

(c) Preparation of a catalyst for obtaining higher yields of tetrahydrofuran in the reaction product.

The operation is carried out exactly as in the preparation of catalyst A but, in addition to the 120 g hydrated nickel nitrate, zirconium oxychloride in aqueous solution is added in such an amount that an atomic ratio of zirconium to nickel of 0.01 is obtained. The remainder of the preparation treatment is effected as for the preparation of catalyst A. This zirconium catalyst is hereinafter referred to as "catalyst C". The specific surface area of this catalyst is 140 m²/g.

EXAMPLE 2

Preparation of BD and THF in a solvent medium comprising gamma-butyrolactone mixed with dioxan or tetrahydrofuran.

10 kg (102 moles) maleic anhydride, 10 kg (116.17 moles) gamma-butyrolactone, 20 kg (226.99 moles) dioxan and 4 kg of catalyst A are introduced into a 50-liter autoclave equipped with an external heat exchanger and a circulation pump. After the reactor has been flushed out with nitrogen and then with hydrogen, the circulation pump is put into operation, a hydrogen pressure of 50 bars is established and heating is started. After 20 minutes, a temperature of 200° C. is reached and, starting from that moment, hydrogen is introduced so as to maintain a constant pressure of 95 bars throughout the test. The temperature is kept constant at 200°±1° C.

The process of the reaction is followed by taking and analyzing samples of the reaction mixture. In this way, it is found that the gamma-butyrolactone content passes through a maximum of 14.9 kg (173 moles) after about 1 hour and drops back to its initial value of 10 kg after 4 hours. At this moment, the autoclave is cooled to about 30° C. and its contents are emptied out after the pressure has been released. The catalyst is filtered off from the reaction product and the latter is subjected to analysis, the results of which are given in the Table below:

|  | kg | moles |
|---|---|---|
| succinic anhydride(*) | 0.173 | 1.73 |

|  | kg | moles |
|---|---|---|
| 1,4-butanediol | 6.894 | 76.5 |
| tetrahydrofuran | 1.103 | 15.3 |
| gamma-butyrolactone | 10 | 116.17 |
| propanol | 0.245 | 4.08 |
| butanol | 0.198 | 2.75 |
| dioxan | 20 | 226.99 |

(*)Conversion of the maleic anhydride is 100%, the acid value subsisting in the reaction product is supplied by the succinic anhydride formed.

The molar % yields obtained are as follows:

| succinic anhydride: | 1.73/102 × 100 = 1.7 mol % |
|---|---|
| 1,4-butanediol: | 765/102 × 100 = 75 mol % |
| tetrahydrofuran: | 15.3/103 × 100 = 15 mol % |
| gamma-butyrolactone: | (116.17−116.17)/102 × 100 = 0 mol % |
| propanol + butanol: | (4.08 + 2.75)/102 × 100 = 6.7 mol % |

Instead of 20 kg dioxan, it is possible to use 20 kg tetrahydrofuran. The procedure is exactly as described above and the same results are obtained except that the reaction is a little slower (4.3 hours instead of 4 hours).

EXAMPLE 3

Preparation of gamma-butyrolactone in situ.

The operation is carried out under the same conditions as in Example 2 but 20 kg (204.08 moles) maleic anhydride, 20 kg dioxan and 4 kg catalyst A are introduced into the 50-liter autoclave. After hydrogenolysis for 4 hours, the following products are obtained, in addition to dioxan and the catalyst:

|  | kg | moles |
|---|---|---|
| succinic anhydride | 0.408 | 4.08 |
| 1,4-butanediol | 6.07 | 67.35 |
| tetrahydrofuran | 0.736 | 10.2 |
| gamma-butyrolactone | 10 | 116.17 |
| propanol | 0.122 | 2.04 |

Converted into molar % yields, these results are as follows:

| succinic anhydride: | 4.08/204.08 × 100 = 2 |
|---|---|
| 1,4-butanediol: | 67.35/204.08 × 100 = 33 |
| tetrahydrofuran: | 10.2/204.08 × 100 = 5 |
| gamma-butyrolactone: | 116.17/204.08 × 100 = 56.9 |
| propanol: | 2.04/204.08 × 100 = 1. |

If the butanediol and the tetrahydrofuran are separated and 10 kg of fresh maleic anhydride are added, a solution is obtained which is quite similar to the starting reaction mixture of Example 2 but with the difference that here the gamma-butyrolactone has been formed in situ in a previous stage, whereas in Example 2 this substance was added directly at the outset.

If the solution obtained in the present Example (without BD and without THF but with an additional 10 kg maleic anhydride) is subjected to hydrogenolysis, the same results are obtained as in Example 2 and 10 kg gamma-butyrolactone, which can be used as solvent in a subsequent reaction, are recovered again and so on.

Instead of the 20 kg dioxan, it is also possible to use 20 kg tetrahydrofuran for the preparation of the 10 kg gamma-butyrolactone in situ. The results are still the same but the reaction is a little slower: 4.3 hours instead of 4 hours for dioxan.

EXAMPLE 4

Preparation of 1,4-butanediol and tetrahydrofuran in gamma-butyrolactone as the sole solvent medium.

20 kg (204.08 moles) maleic anhydride, 24 kg gamma-butyrolactone and 4 kg catalyst A are used for the test and the hydrogenolysis is effected under the same conditions as regards equipment, temperature and pressure as in Example 2. After hydrogenolysis for 8 hours, the following yields in mol % are obtained:

| 1,4-butanediol | 74 |
|---|---|
| tetrahydrofuran | 14 |
| gamma-butyrolactone | 0* |
| propanol + butanol | 4.1 |

*The reaction time (8 hours) was selected so that, at the end of this period the reaction product contains exactly the 24 kg gamma-butyro-lactone initially added as reaction medium; the yield of gamma-butyro-lactone, is therefore, 0 mol % under these conditions.

When Examples 2 and 4 are compared, the following is found:

whatever the solvent medium used, the yields of BD and THF are substantially the same;

the speed of hydrogenolysis is as follows in decreasing order: dioxantetrahydrofuran - gamma-butyrolactone;

however, tetrahydrofuran and gamma-butyrolactone have the advantage of not introducing into the reaction a product extraneous to the latter, unlike dioxan.

EXAMPLE 5

Modification of the ratio BD/THF.

In this Example, it is shown that, by adding niobium (catalyst B) or zirconium (catalyst C) to the Ni/Mo catalyst, it is possible to modify the ratio BD/THF in the reaction product obtained.

The reaction conditions are those of Example 2 (T=200° C., P=95 bars) and, in this way, the following yields are obtained (in mol %):

|  | Catalyst B | Catalyst C |
|---|---|---|
| reaction time (hours) | 4.3 | 4.0 |
| succinic anhydride | 1.5 | 1.5 |
| 1,4-butanediol | 55 | 40 |
| tetrahydrofuran | 35 | 50 |
| gamma-butyrolactone | 0 | 0 |
| propanol + butanol | 6 | 6.5 |

EXAMPLE 6

Influence of the amount of catalyst.

In Example 2, the weight ratio between the amount of catalyst and the amount of maleic anhydride is 0.4. If this ratio is lowered to a value of 0.25, the following molar % yields are obtained, other conditions being the same as in Example 2:

reaction time: 6.5 hours (instead of 4 hours)
yield of succinic anhydride: 1.7 (status quo)
yield of 1,4-butanediol: 75 (status quo)
yield of tetrahydrofuran: 15 (status quo)
yield of gamma-butyrolactone: 0 (status quo)
yield of propanol+butanol: 6.5 (instead of 6.7).

In conclusion, apart from the longer reaction time, practically the same yields are obtained.

EXAMPLE 7

Influence of the gamma-butyrolactone content in the initial reaction mixture.

The operation is carried out under the same conditions as in Example 2 but varying the weight ratio of maleic anhydride to gamma-butyrolactone.

In Example 2, this ratio was 1/1, whereas in the present Example, a ratio of 2/1 (according to the present invention) and a ratio of 13/1 (which therefore is outside the range of from 1/1 to 4/1 according to the present invention) are used, respectively, the balance of raw materials thus being as follows (in kg):

|  | Ratio 1/1 (Example 2) | Ratio 2/1 | Ratio 13/1 |
| --- | --- | --- | --- |
| maleic anhydride | 10 | 16 | 32.5 |
| gamma-butyrolactone | 10 | 8 | 2.5 |
| dioxan | 20 | 16 | 5 |
| catalyst A | 4 | 4 | 4 |
| In each test: | | | |
| T = 200° C. and P = 95 bars. | | | |

The following yields are obtained (in mol %):

|  | Ratio 1/1 (Example 2) | Ratio 2/1 | Ratio 13/1 |
| --- | --- | --- | --- |
| reaction time (hours) | 4 | 6.5 | 13 |
| succinic anhydride | 1.7 | 1.7 | 1.3 |
| 1,4-butanediol | 75 | 70 | 53 |
| tetrahydrofuran | 15 | 20 | 26 |
| gamma-butyrolactone | 0 | 0 | 0 |
| propanol + butanol | 6.7 | 6.5 | 18 |

It can, therefore, be seen that, below the range according to the invention (1:1 to 4:1), (a) the yield of butanediol decreases considerably, (b) the yield of by-products (propanol+butanol) on the other hand is almost trebled, and (c) the reaction time is doubled to trebled, depending on the case.

EXAMPLE 8

Influence of double oxidizing thermal treatment on stability of catalyst activity.

In the following tests, use is made of a catalyst A prepared exactly as described in Example 1 and a catalyst X not according to the present invention, prepared from the same raw materials and with the same proportions as those of catalyst A but without effecting the double oxidation according to the present invention. After hydrogenolysis of maleic anhydride according to the present invention, the catalyst is separated from the reaction mixture and its deactivation rate is then measured. The following results are obtained:

|  | First oxidation of the Ni salt into NiO for 3 hours at 450° C. | Second oxidation of NiO + Mo salt for 3 hours at 500° C. | Reduction in H$_2$ for 3 hours at 475° C. | Deactivation rate in % |
| --- | --- | --- | --- | --- |
| Catalyst (A) | yes | yes | yes | 0.23 |
| Catalyst (X) | no | no | yes | 1.7 |

It is seen that the deactivation rate is 8 times less if the double oxidation of the catalyst is carried out before its reduction. In industrial practice, this means that, after each hydrogenolysis, 0.23% by weight of catalyst (A) must be replaced by fresh catalyst (A) before effecting the next hydrogenolysis, whereas with the catalyst (X), 8 times as much of it must be replaced.

Measurement of the deactivation rate of the catalyst is made as follows:

(a) for a series of 20 successive hydrogenolyses with the same catalyst, the reduction of the speed of reaction occurring from the first hydrogenolysis to the twentieth is measured. This reduction is linear. If the speed of reaction of the first hydrogenolysis is designated $V_1$ and the speed of the twentieth is designated $V_{20}$, the reduction of speed is equal to $V_1-V_{20}$ divided by 20, which gives $\Delta V$;

(b) on the other hand, the relation existing between the speed of reaction and the quantity by weight of fresh catalyst is established. This relation makes it possible to convert the reduction of speed of reaction $\Delta V$ into an apparent weight loss of catalyst, designated $\Delta P$;

(c) if P is the weight of fresh catalyst, the deactivation is expressed by $\Delta P/P$.

We claim:

1. A process for the production of 1,4-butanediol and tetrahydrofuran which comprises subjecting maleic anhydride to a single-stage catalytic hydrogenolysis at a temperature of from 170° to 215° C. and a pressure of from 60 to 200 bars in a reaction medium comprising gamma-butyrolactone for a time such that the amount of gamma-butyrolactone present in the final reaction medium is substantially equal to that present in the initial reaction medium, in the presence of a solid reduced catalyst consisting essentially of nickel in association with molybdenum and/or tungsten with or without zirconium and/or niobium, said catalyst being prepared by subjecting a nickel compound to an oxidation treatment by heating in the presence of air at a temperature of from 200° to 500° C. for a period of from 1 to 10 hours, intimately admixing a molybdenum and/or tungsten compound with the resulting nickel oxide, subjecting the mixture thus obtained to calcination by heating in the presence of air at a temperature of from 300° to 700° C. for a period of from 1 to 20 hours and reducing the catalyst thus obtained in a hydrogen atmosphere at a temperature of from 450° to 500° C.

2. The process of claim 1, wherein the pressure is from 75 to 125 bars.

3. The process of claim 1, wherein the nickel, molybdenum, tungsten, zirconium and niobium compounds used in the preparation of the catalyst are compounds which are soluble in water and which can produce respectively metallic nickel, molybdenum, tungsten, zirconium and niobium by thermal reduction.

4. The process of claim 1, wherein the catalyst is supported.

5. The process of claim 4, wherein the catalyst is supported on kieselguhr.

6. The process of claim 1, wherein the nickel compound is nickel carbonate precipitated from an aqueous solution of a nickel salt.

7. The process of claim 1, wherein the oxidation treatment is carried out at a temperature of from 350° to 500° C. for a period of from 2 to 4 hours.

8. The process of claim 1, wherein the calcination is carried out at a temperature of from 450° to 550° C. for a period of from 2 to 4 hours.

9. The process of claim 1, wherein the Mo:Ni or W:Ni atomic ratio is from 0.03 to 0.3.

10. The process of claim 9, wherein the Mo:Ni or W:Ni atomic ratio is from 0.1 to 0.2.

11. The process of claim 9, wherein the Mo:Ni or W:Ni atomic ratio is from 0.11 to 0.13.

12. The process according to claim 1, wherein the catalyst comprises zirconium and/or niobium, the atomic ratio of zirconium and/or niobium to nickel being from 0.001 to 0.1.

13. The process of claim 12, wherein the atomic ratio of zirconium and/or niobium to nickel is about 0.01.

14. The process of claim 1, wherein the specific surface area of the solid reduced catalyst is from 100 m$^2$/g to 165 m$^2$/g.

15. The process of claim 14, wherein the specific surface area of the solid reduced catalyst is from about 140 m$^2$/g to about 150 m$^2$/g.

16. The process of claim 1, wherein the ratio by weight of maleic anhydride to gamma-butyrolactone in the initial reaction medium is between 0.5:1 and 4:1.

17. The process of claim 16, wherein the ratio by weight of maleic anhydride to gamma-butyrolactone in the initial reaction medium is between 0.8:1 and 2:1.

18. The process of claim 1, wherein the reaction medium comprises a co-solvent selected from the group consisting of dioxan and tetrahydrofuran.

19. The process of claim 17, wherein the ratio by weight of gamma-butyrolactone to co-solvent is within the range of from 1:0 to 1:7.

20. The process of claim 17, wherein the ratio by weight of gamma-butyrolactone to co-solvent is within the range of from 1:2 to 1:4.

21. The process of claim 1, wherein the amount of catalyst used is from 10 to 40 parts by weight per 100 parts by weight of maleic anhydride.

22. The process of claim 21, wherein the amount of catalyst used is from 20 to 40 parts by weight per 100 parts by weight of maleic anhydride.

23. The process of claim 21, wherein the catalytic hydrogenolysis is carried out in a loop reactor.

24. The process of claim 1 wherein said zirconium and/or niobium compound is added to the nickel compound or to the molybdenum and/or tungsten compound.

* * * * *